United States Patent
Kim et al.

(10) Patent No.: US 9,286,700 B2
(45) Date of Patent: Mar. 15, 2016

(54) METHOD FOR ACQUIRING PET IMAGE WITH ULTRA-HIGH RESOLUTION USING MOVEMENT OF PET DEVICE

(71) Applicant: GACHON UNIVERSITY OF INDUSTRY-ACADEMIC COOPERATION FOUNDATION, Gyeonggi-do (KR)

(72) Inventors: Hang Keun Kim, Incheon (KR); Young Don Son, Gyeonggi-do (KR); Zang Hee Cho, Incheon (KR); Young Bo Kim, Gyeonggi-do (KR); Dae Hyuk Kwon, Seoul (KR); Yo Han Joo, Incheon (KR)

(73) Assignee: GACHON UNIVERSITY OF INDUSTRY-ACADEMIC COOPERATION FOUNDATION, Gyeonggi-Do (KR)

( * ) Notice: Subject to any disclaimer, the term of this patent is extended or adjusted under 35 U.S.C. 154(b) by 0 days.

(21) Appl. No.: 14/359,602

(22) PCT Filed: Mar. 15, 2013

(86) PCT No.: PCT/KR2013/002106
§ 371 (c)(1),
(2) Date: May 21, 2014

(87) PCT Pub. No.: WO2013/162172
PCT Pub. Date: Oct. 31, 2013

(65) Prior Publication Data
US 2015/0034830 A1    Feb. 5, 2015

(30) Foreign Application Priority Data
Apr. 27, 2012 (KR) .......... 10-2012-0044408

(51) Int. Cl.
G06T 11/00 (2006.01)
G01T 1/29 (2006.01)
A61B 6/03 (2006.01)
A61B 6/00 (2006.01)

(52) U.S. Cl.
CPC ............ *G06T 11/005* (2013.01); *A61B 6/037* (2013.01); *A61B 6/4258* (2013.01); *A61B 6/4275* (2013.01); *G01T 1/2985* (2013.01); *G06T 2211/416* (2013.01); *G06T 2211/424* (2013.01)

(58) Field of Classification Search
CPC ............ G01T 1/2985; G06T 11/005; G06T 2211/416; G06T 2211/424; A61B 6/037; A61B 6/4258; A61B 6/4275
See application file for complete search history.

(56) References Cited

U.S. PATENT DOCUMENTS

| 2007/0053486 A1* | 3/2007 | Zelnik et al. ............... 378/20 |
| 2008/0063247 A1 | 3/2008 | Griswold |
| 2009/0253980 A1 | 10/2009 | Wollenweber |
| 2011/0268334 A1* | 11/2011 | Ra et al. .................. 382/131 |

FOREIGN PATENT DOCUMENTS

| JP | 2002-357567 | 12/2002 |
| KR | 10-2011-0121536 | 11/2011 |
| KR | 10-2011-0130962 | 12/2011 |

* cited by examiner

*Primary Examiner* — David Porta
*Assistant Examiner* — Mindy Vu
(74) *Attorney, Agent, or Firm* — Gottlieb, Rackman & Reisman, P.C.

(57) ABSTRACT

A method for acquiring a PET image with ultra high resolution using movement of a PET device is provided. In the related art, there is a limit in lowering of the resolution below a half (d/2) of the width of a detector. According to the provided method, an image with ultra high resolution, which can jump over the limit, can be acquired. Further, since utilization of larger detectors becomes possible without a loss of the resolution, the sensitivity of the PET can be improved, and thus an image of higher quality can be acquired.

5 Claims, 6 Drawing Sheets (a)  (b)

(a)  (b)

METHOD FOR ACQUIRING PET IMAGE WITH ULTRA-HIGH RESOLUTION USING MOVEMENT OF PET DEVICE

TECHNICAL FIELD

The present invention relates to a method for acquiring a PET image with ultra high resolution using movement of a PET device.

BACKGROUND ART

Recently, with the increase of importance of a bin-functional image, importance of PET (Positron Emission Tomography) is greatly increasing. However, the PET has a limit that it is basically difficult to lower the resolution below a half (d/2) of the width (d) of a detector. This will be described with reference to FIG. 1.

According to the PET, if a positron is emitted from a specific pixel, two destroyed photons of 511 KeV are generated and proceed, being separated from each other at an angle of 180 degrees, and are detected by two detectors which stand opposite to each other. The probability that the positron emission in a specific pixel is detected on a response curve that is composed of two specific detectors is called CRF (Coincidence Response Function).

As illustrated as (1) of FIG. 1, an ideal point detector corresponds to a point, and as illustrated as (2) and (3) of FIG. 1, an ideal line of response (LOR) corresponds to an ideal line.

However, a detector of finite extent has a width (d) due to its constant volume as illustrated as (2) and (3) of FIG. 1, and the line of response is not an ideal line as illustrated as (2) of FIG. 1, but has a geometrical CRF as illustrated as (3) of FIG. 1.

(3) of FIG. 1 illustrates the CRF in consideration of only geometrical elements except for other physical variables. Red color indicates high detection probability, and blue color indicates low detection probability. By the geometrical analysis as illustrated in FIG. 1, it is not possible to obtain the resolution that is lower than a half (d/2) of the width of the detector.

Further, as the size of the detector becomes smaller, the sensitivity of the system is greatly degraded, and there is a limit in obtaining a high resolution image.

To overcome this, a fusion imaging system such as PET-CT or PET-MR has been introduced. However, the performance of the PET itself is limited, and this exerts an influence on the fusion imaging system.

The related art related to this issue may be examined as follows.

KR 10-2011-0121536 A discloses a method for obtaining a high resolution image, which moves a PET detector itself or a bed, measures the degree of motion and detects an image signal that is differently detected depending on the motion, and reconstructs a corresponding PSF. However, according to this related art, the high resolution image is not acquired using a plurality of low resolution images, but is acquired through preprocessing or post-processing of the image.

KR 10-2011-0121535 A, JP 2001-330671 A, and U.S. Pat. No. 8,103,487 B disclose methods to improve resolution by reconstructing images without movement of a PET detector itself or a bed.

(Patent Document 1) KR 10-2011-0121536 A
(Patent Document 2) KR 10-2011-0121535 A
(Patent Document 3) JP 2001-330671 A
(Patent Document 4) U.S. Pat. No. 8,103,487 B

DISCLOSURE

Technical Problem

An aspect of the present invention provides an apparatus for obtaining a PET image with ultra high resolution and a method for reconstructing an image, which can overcome the limit of spatial resolution due to the size of a detector in PET.

In particular, the present invention is to maintain ultra high resolution by overcoming the limit of the size of the detector in the spatial resolution and to improve the sensitivity of a PET system.

Technical Solution

According to one aspect of the present invention, there is provided a method for acquiring a PET image with ultra high resolution using movement of a PET device, which includes (a) a driving member 30 driving the PET device by a driving control unit 100; (b) performing sampling p times for respective detectors 11 by driving of the PET device, and a PET signal receiving unit 200 receiving a plurality of PET data; (c) are image reconstructing unit 300 acquiring the PET data acquired from the PET signal receiving unit 200, and acquiring position information of the PET device from the driving control unit 100; and (d) the image reconstructing unit 300 reconstructing an image using the acquired PET data and the position information.

Driving of the PET device may be driving of a gantry 10 or a bed 20 of the PET device.

Further, driving of the PET device may be driving in a unit that is smaller than a half (d/2) of a width of the detector 11.

The step (d) may be performed in an iterative method that corrects an existing pixel value $X^{old}_j$ to a new pixel value $X^{new}_j$ using the acquired PET data and the position information.

The iterative method may iterate acquiring a translation operation value $T_p$ that is the position information, obtaining a correction factor sinogram by performing forward projection, and then returning to coordinates of the original image by performing backward projection.

Advantageous Effects

In accordance with the present invention, the image with ultra high resolution, which can jump over the limit in size of the detector, can be acquired.

In accordance with the present invention, utilization of larger detectors becomes possible without a loss of resolution and thus the sensitivity of the PET can be improved.

Further, sampling in a dead space, which occurs due to a gap between detectors, becomes possible, and thus an image of higher quality can be acquired.

Even through such a work, there is no loss of the data operation speed.

DESCRIPTION OF REFERENCE NUMERALS IN THE DRAWINGS

- 10: gantry
- 11: detector
- 20: bed
- 30: driving member
- 100: driving control unit
- 200: PET signal receiving unit
- 300: image reconstructing unit

BEST MODE

Hereinafter, "ultra high resolution" means resolution having a value that is smaller than a half (d/2) of a width of a detector to overcome a geometrical limit of the half (d/2) of the width of the detector as described above.

Figure 1:
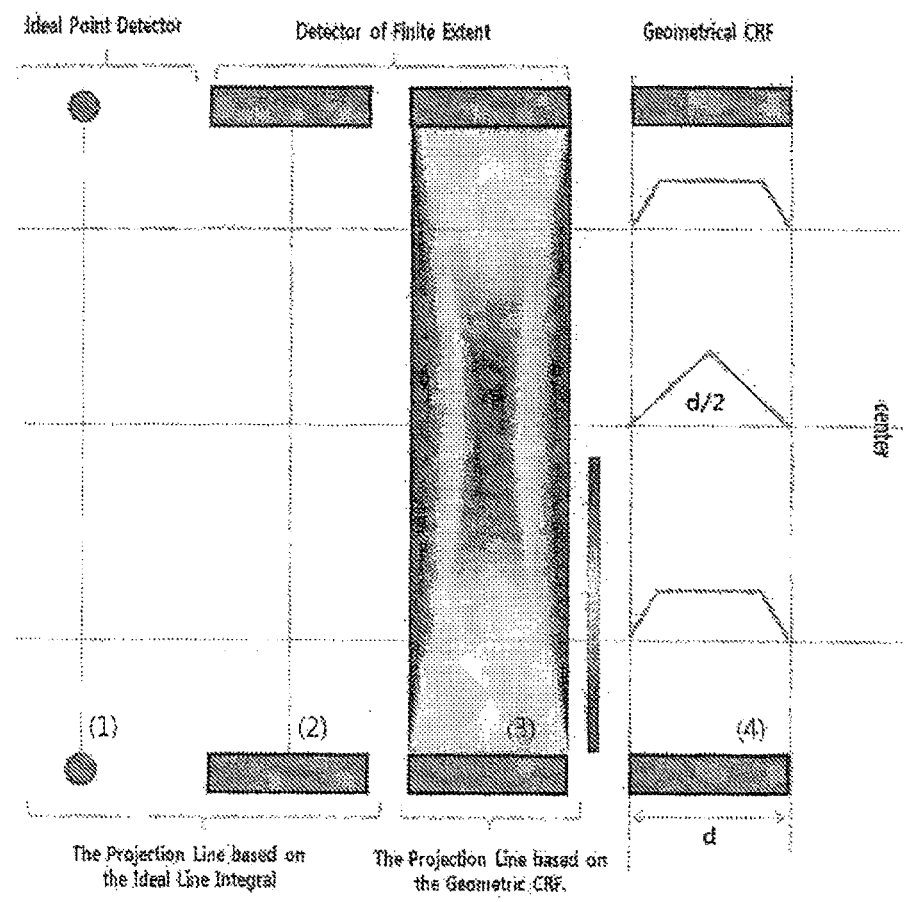
FIG. 1 is a conceptual diagram explaining a limit of resolution of a PET image by geometrical analysis.
Figure 2:
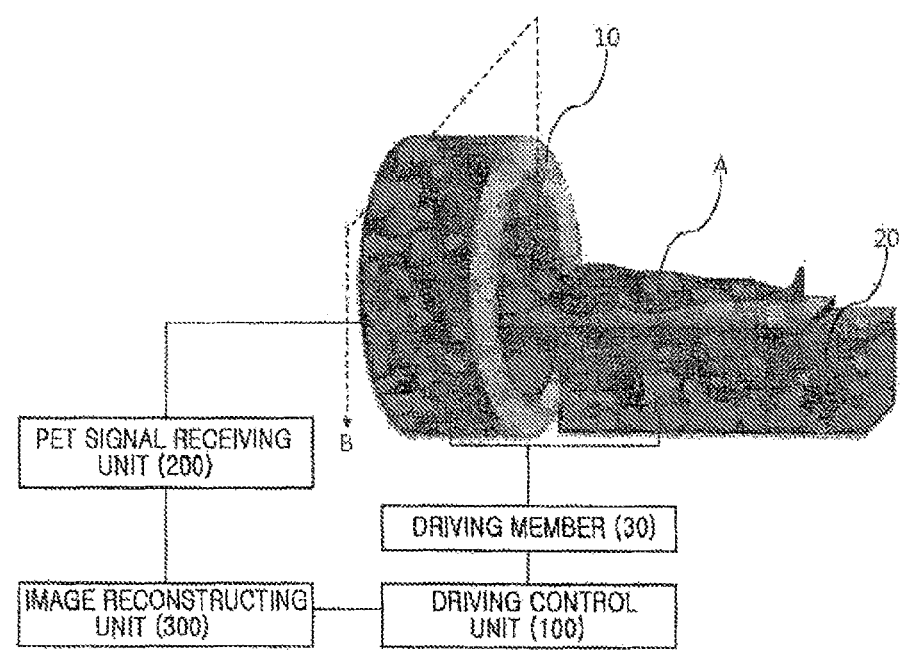
FIG. 2 is a diagram illustrating the configuration of an apparatus for acquiring a PET image with ultra high resolution according to the present invention.

Referring to FIG. 1, an apparatus for acquiring a PET image with ultra high resolution according to the present invention will be briefly described.

Like a PET device in the related art, a PET device includes a gantry 10 that is a structure on which detectors 11 are installed and a bed 20 on which a photographing target A is located. The PET device can be driven by a driving member 30, such as a motor.

A driving target may be any one of the gantry 10 and the bed 20. To be described layer, for image reconstruction, the driving interval thereof should be shorter than a half (d/2) of a width of the detector 11. In one embodiment, the gantry 10 may perform a wobbling movement.

A driving control unit 100 may control the operation of the PET device by controlling the operation of the driving member 30 through an input of a driving parameter. Further, the driving control unit 100 may transmit the driving parameter to an image reconstructing unit 300 so that the driving parameter can be used as input data for a PET image with ultra high resolution.

A PET signal receiving unit 200 receives and stores PET data from the detectors 11 of the gantry 10, and transmits the PET data to the image reconstructing unit 300. In particular, the PET signal receiving unit 200 may store position information of the gantry 10 that is moved by the driving member 30 and the PET data obtained from the respective detectors 11 when the gantry 10 is in respective positions.

The PET data may be stored as one listmode data or as listmode or sinogram data for the respective positions.

The listmode data is data having measurement time information, and position information of the gantry 10 may be added thereto. The addition of the position information may be performed by processing and storing relative offsets together with the existing information of the detectors 11 or by adding new tags to the existing information of the detectors 11.

In the case of storing the PET data as the listmode data, the PET data is generally formed as sinogram data through rebinning and histogramming.

At present, in the case of a general PET, L64 data is data having time information and information of the corresponding detectors, and L32 data is obtained by changing the information of the two detectors, which form one line of response (LOR) through rebinning, to corresponding address values. Sinograms are obtained by removing the time information from the L32 data and changing the L32 data to a form that is frequently used to reconstruct tomography.

According to the present invention, although sinograms are acquired as many as the number of positions used during sampling, L64 data can be obtained and processed in parallel (see FIG. 6), and can be stored in parallel as the sinograms or list modes (L64 or L32) in the PET signal receiving unit 200. Accordingly, although a larger storage space is necessary, the data processing time is not so long in processing a large amount of data.

The image reconstructing unit 300 acquires the PET image with ultra high resolution by reconstructing the image using the PET data received from the PET signal receiving unit 200 and the driving parameter received from the driving control unit 100. Hereinafter, the method for reconstructing the image will be described in detail.

The driving of the apparatus for acquiring a PET image with ultra high resolution will be described in more detail.

FIG. 3(a) illustrates a state where the apparatus for acquiring a PET image with ultra high resolution is not driven, and FIG. 3(b) illustrates a state where the apparatus for acquiring a PET image is driven.

FIG. 3(b) illustrates wobbling as an example of the driving.

The illustrated wobbling is sampled at four positions, which are discriminated by colors. The number of samplings is not limited, but if the number is too large, the data throughput is increased, and it takes a lot of time in acquiring the PET image. Accordingly, it is preferable that the number of samplings is appropriately adjusted.

Figure 3:
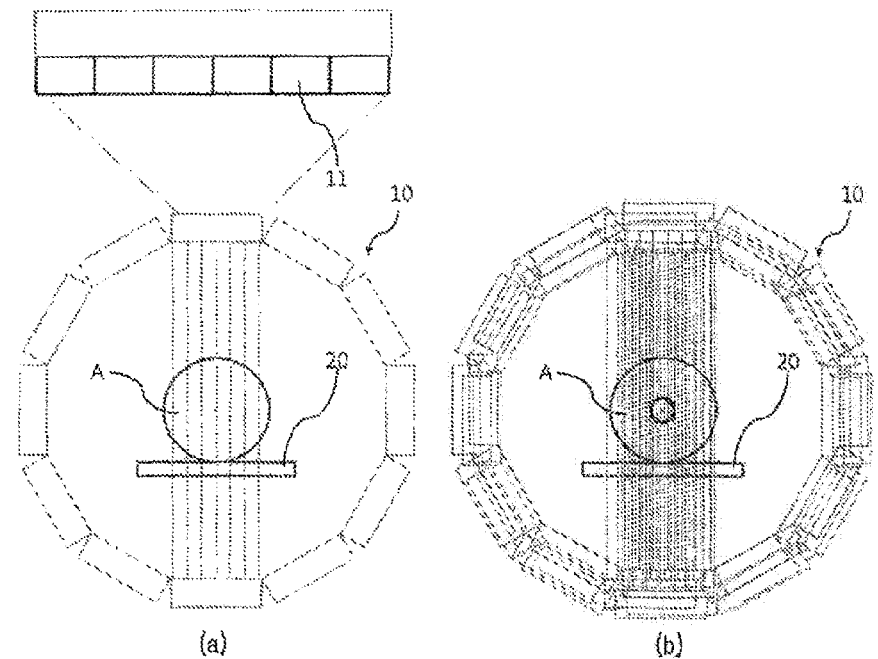
FIGS. 3 and 4 are conceptual diagrams explaining driving of a PET device according to the present invention.
Figure 4:
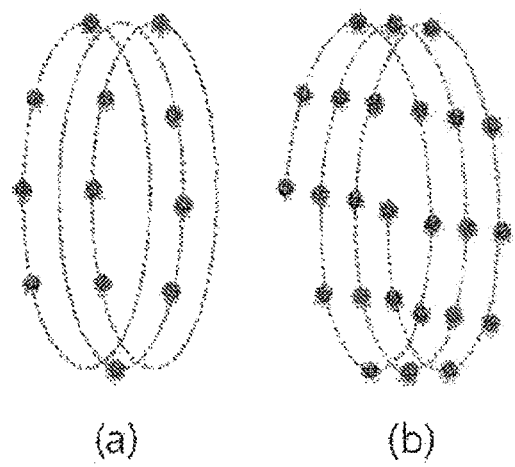

3D sampling becomes possible through combination of movements shown in FIG. 3, which is illustrated in FIG. 4. The combination form may be circular or trajectory.

Figure 5:
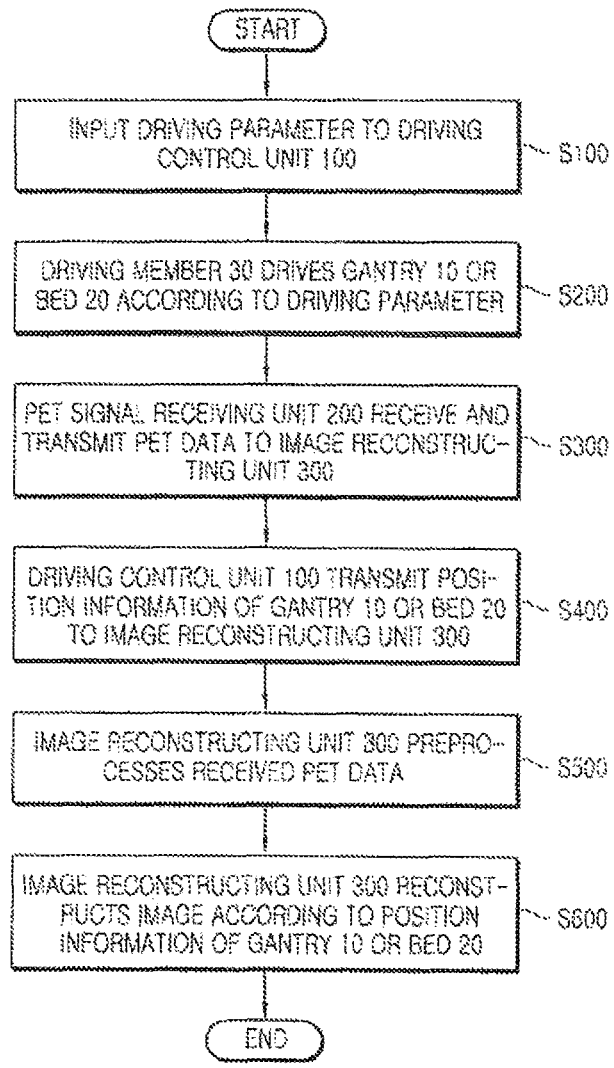
FIG. 5 is a flowchart illustrating a method for acquiring a PET image with ultra high resolution according to the present invention.

Referring to FIG. 5, the method for acquiring a PET image with ultra high resolution according to the present invention will be described.

First, if the driving parameter is input to the driving control unit 100 (S100), the driving control unit 100 controls the driving member 30 to drive the gantry 10 or the bed 20 (S200).

The PET device is operated, and the PET signal receiving unit 200 receives the PET data according to the driving of the PET device and transmits the PET data to the image reconstructing unit 300 (S300).

On the other hand, the image reconstructing unit 300 receives position information of the gantry 10 or the bed 20 from the driving control unit 100 (S400).

The image reconstructing unit 300 preprocesses the received PET data (S500), and then reconstructs the image with ultra high resolution using the transmitted position information.

The method for reconstructing the image with ultra high resolution, which is performed by the image reconstructing unit 300, will be described in detail.

Basically, the reconstruction of the image is performed based on an iterative method for iterating forward projection and backward projection using a system matrix that is constructed by probabilities detected from the respective LORs of pairs of detectors 11.

The forward projection is an operation to convert the PET data that is data in an image form into data in a sinogram form, and the backward projection is an operation to convert data in a sinogram form into data in an image form. On the other hand, a set of probability coefficients that are used when the forward projection and the backward projection are performed is the system matrix.

According to the iterative method for acquiring the PET image with ultra high resolution according to the present invention, the system matrix is made by calculating probabilities that positron emission, which occurs at specific coordinates of the image, is detected in a specific LOR in consideration of the statistical characteristic of the PDT measurement or various physical or geometrical characteristics, and using this, the forward projection and the backward projection are iteratively performed.

Any iterative method may be used, and according to an embodiment of the present invention, a method for correcting initial image data is used, in which data in a sinogram form is made by performing forward projection with respect to initial image data, a correction factor sinogram for correcting the degree of a difference is obtained by comparing the made sinogram with the sinogram measured in the actual PET, and data in an image form is constructed by performing backward projection with respect to the correction factor sinogram.

Through the continuous iteration of the above-described operation, an image that corresponds to the measured sinogram is obtained.

Figure 6:
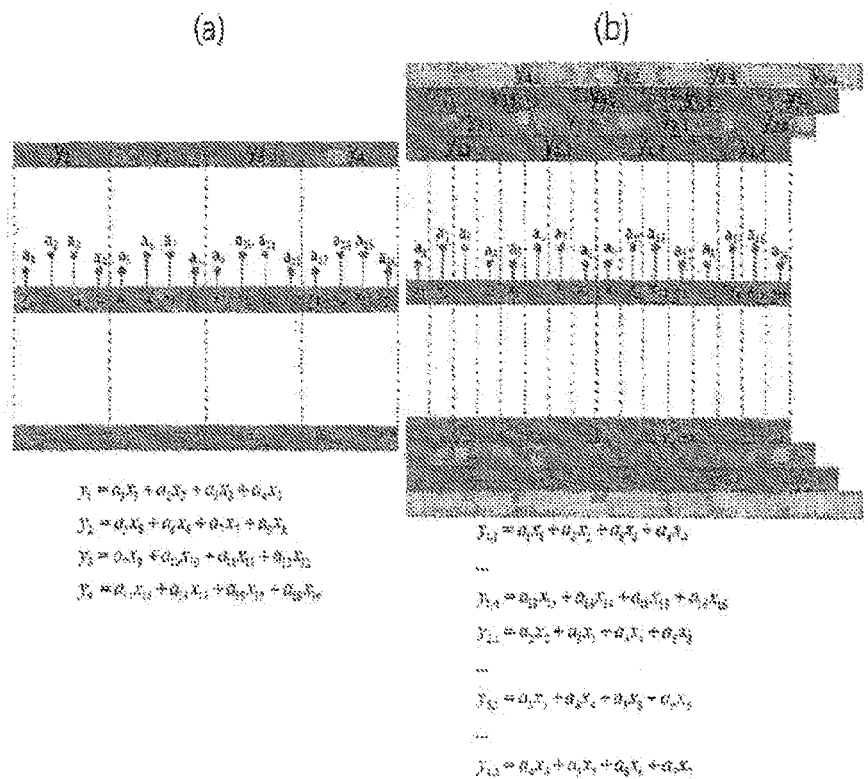
FIG. 6 is a conceptual diagram explaining the principle of acquiring a PET image with ultra high resolution by movement of a PET device.

Referring to FIG. 6, this will be described in more detail.

FIG. 6(a) illustrates a state where the PET device is not driven. $a_i$ denotes a probability that the position emission at a pixel is detected at the i-th LOR (or sinogram bin), $x_j$ denotes the number of positron emissions occurring at the j-th pixel, and $y_i$ denotes the number of positron emissions in the detector 11 that is detected at the i-th sinogram bin.

As illustrated in FIG. 6(a), in the case of the existing PET device that receives the positron emission at one position, four equations are obtained through the measurement.

Equation 1 is an equation related to forward projection performance in the case where the gantry 10 or the bed 20 moves as shown in FIG. 6(b), and expresses a state where the iterative method is not performed.

$$y_i = \sum_{i}^{M} a_{ij} x_j \quad \text{[Equation 1]}$$

Here, M denotes the number of all pixels, $a_{ij}$ denotes a system matrix that is a probability that the positron emission at the j-th pixel is detected at the i-th LOR. (or sinogram bin), $x_j$ denotes a pixel value that is the number of positron emissions occurring at the j-th pixel, and $y_i$ denotes the number of positron emissions that is detected at the i-th sinogram bin.

Based on Equation 1, a method for correcting an existing pixel value $X^{old}_j$ to a new pixel value $X^{new}_j$ through a simple iterative method without driving of the PET device as in FIG. 6(a) can be expressed by Equation 2 below.

$$x^{new}_j = x^{old}_j \frac{1}{\sum_{i=1}^{N} a_{ij}} \sum_{i=1}^{N} \frac{a_{ij} y_i}{\sum_{k=1}^{M} a_{ik} x^{old}_k} \quad \text{[Equation 2]}$$

Here, $X^{new}_j$ denotes the j-th pixel value to be newly obtained, $X^{old}_j$ denotes the existing j-th pixel value, N denotes the total number of sinogram bins, and M denotes the total number of image pixels.

Now, a method for acquiring an image with ultra high resolution according to the driving of the gantry 10 or the bed 20 according to the first embodiment of the present invention will be described.

FIG. 6(b) illustrates a case where the gantry 10 or the bed 20 is moved to four positions and sampling is performed. 16 equations are obtained, and the sum of weighting values of respective pixels can be obtained. By iterating the PET data obtained at various positions, pixel values that are smaller than the size of the detector can be obtained.

That is, in the case of performing sampling while moving p times (p=4 in FIG. 6(b)). Equation 3 below may be applied thereto.

$$x^{new}_j = x^{old}_j T_p^{-1} \left[ \frac{1}{\sum_{i=1}^{N} a_{ij}} \sum_{i=1}^{N} \frac{a_{ij} y_{pi}}{\sum_{k=1}^{M} a_{ik} T_p [x^{old}_k]} \right] \quad \text{[Equation 3]}$$

Here, P denotes sampling positions in the same detector 11 according tot the driving of the gantry 10 or the bed 20, $y_{pi}$ denotes the i-th bin value of the sinogram measured at the p-th position, and $y_{pi}$ denotes a translation operation value.

As compared with Equation 2, Equation 2 uses the fixed whereas Equation 3 according to the present invention uses $y_{pi}$ according to p positions, and includes a translation operation value $T_p$ of a translation that describes the movement of the gantry 10 or the bed 20 in each case.

That is, in order to calculate the correction factor, the translation operation value $T_p$ that describes the movement of the gantry 10 or the bed 20 is acquired with respect to a predicted value x of the current image, a correction factor sonogram is obtained by performing forward projection, the coordinates of the original image is returned by performing backward projection $T_p^{-1}$, and then the predicted image is multiplied by the result of the operation.

In the method according to the present invention, p times update of the measurement points is performed for once iteration. That is, the amount of computation is increased as much as the number (p) of measurement positions.

However, as the result of imaging, the quality of the image, which can be obtained by p times iteration in the existing method, can be obtained only by once iteration, there is no loss of the operation speed as described above.

According to a method for acquiring an image with ultra high resolution according to the driving of the gantry 10 or the bed 20 according to the second embodiment of the present invention, the update is not performed for respective positions, but is performed through averaging. This method is expressed in Equation 4.

$$x^{new}_j = \frac{1}{P} \sum_{p=1}^{P} x^{old}_j T_p^{-1} \left[ \frac{1}{\sum_{i=1}^{N} a_{ij}} \sum_{i=1}^{N} \frac{a_{ij} y_{pi}}{\sum_{k=1}^{M} a_{ik} T_p [x^{old}_k]} \right] \quad \text{[Equation 4]}$$

Figure 7:
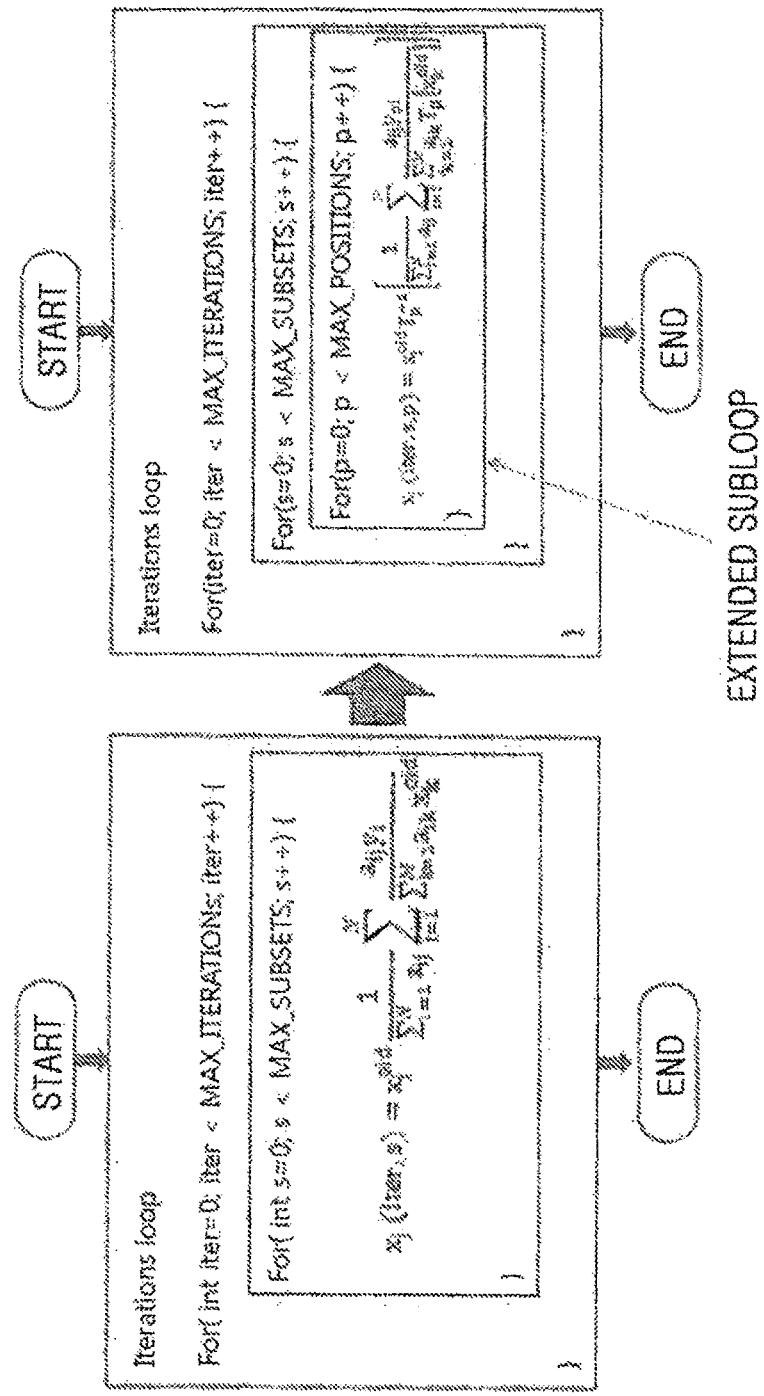
FIG. 7 is a flowchart illustrating a method for acquiring a PET image with ultra high resolution according to a third embodiment of the present invention.

A method for acquiring an image with ultra high resolution according to the driving of the gantry 10 or the bed 20 according to the third embodiment of the present invention may use a loop structure as shown in FIG. 7.

In the loop structure illustrated in FIG. 7, one sinogram is divided into a. plurality of subsets. Through this method, the speed can be improved.

The scope of the present invention is defined by the appended claims rather than the detailed description as described above, and it will be construed that all corrections and modifications derived from the meanings and scope of the following claims and the equivalent concept fall within the scope of the present invention.

The invention claimed is:

1. A method for acquiring a PET image with ultra high resolution using movement of a PET device, comprising:

(a) a driving member 30 driving the PET device by a driving control unit 400;

(b) performing sampling p times for respective detectors 44 by driving of the PET device, and a PET signal receiving unit 200 receiving a plurality of PET data;

(c) an image reconstructing unit 300 acquiring the PET data acquired from the PET signal receiving unit 200, and acquiring position information of the PET device from the driving control unit 400; and (d) the image reconstructing unit 300 reconstructing an image using the acquired PET data and the position information, wherein the step (d) is performed in an iterative method that corrects an existing pixel value $X^{old}_j$ to a new pixel value $X^{new}_j$ using the acquired PET data and the position information, wherein the iterative method iterates acquiring a translation operation value Tp that is the position information, obtaining a correction factor sinogram by performing forward projection, and then returning to coordinates of the original image by performing backward projection.

2. The method for acquiring a PET image with ultra high resolution of claim 1, wherein driving of the PET device is driving of a gantry or a bed of the PET device.

3. The method for acquiring a PET image with ultra high resolution of claim 1, wherein driving of the PET device is driving in a unit that is smaller than a half (d/2) of a width of the detector.

4. The method for acquiring a PET image with ultra high resolution of claim 1, wherein the iterative method in step (d) is performed by iteratively applying a following equation, $$x_j^{new} = x_j^{old} T_p^{-1} \left[ \frac{1}{\sum_{i=1}^{N} a_{ij}} \sum_{i=1}^{N} \frac{a_{ij} y_{pi}}{\sum_{k=1}^{M} a_{ik} T_p[x_k^{old}]} \right]$$

where, M denotes the number of all pixels, $a_{ij}$ denotes a system matrix that is a probability that the positron emission at the j-th pixel is detected at the i-th sinogram bin, N denotes the total number of sinogram bins, M denotes the total number of image pixels, P denotes sampling positions in the detector according to the driving of the PET device, and $y_{pi}$ denotes the i-th bin value of the sinogram measured at the p-th position.

5. The method for acquiring a PET image with ultra high resolution of claim 1, wherein the iterative method in step (d) is performed by iteratively applying a following equation, $$x_j^{new} = \frac{1}{P} \sum_{p=1}^{P} x_j^{old} T_p^{-1} \left[ \frac{1}{\sum_{i=1}^{N} a_{ij}} \sum_{i=1}^{N} \frac{a_{ij} y_{pi}}{\sum_{k=1}^{M} a_{ik} T_p[x_k^{old}]} \right]$$

where, M denotes the number of all pixels, $a_{ij}$ denotes a system matrix that is a probability that the positron emission at the j-th pixel is detected at the i-th sinogram bin, N denotes the total number of sinogram bins, M denotes the total number of image pixels, P denotes sampling positions in the detector according to the driving of the PET device, and $y_{pi}$ denotes the i-th bin value of the sinogram measured at the p-th position.

* * * * *